United States Patent
Jones et al.

(10) Patent No.: US 6,953,468 B2
(45) Date of Patent: Oct. 11, 2005

(54) OCCLUDING VASCULATURE OF A PATIENT USING EMBOLIC COIL WITH IMPROVED PLATELET ADHESION

(75) Inventors: Donald K. Jones, Lauderhill, FL (US); Vladimir Mitelberg, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 331 days.

(21) Appl. No.: 09/880,506

(22) Filed: Jun. 13, 2001

(65) Prior Publication Data

US 2003/0004531 A1 Jan. 2, 2003

(51) Int. Cl.7 .............................................. A61M 29/00
(52) U.S. Cl. ..................... 606/191; 606/194; 606/200
(58) Field of Search ........................... 606/191, 194, 606/198, 200, 213, 214, 151; 140/92.1, 89; 623/1.1, 901, 902, 903; 128/898

(56) References Cited

U.S. PATENT DOCUMENTS

| | | | |
|---|---|---|---|
| 4,923,460 A | | 5/1990 | Amit |
| 5,163,958 A | | 11/1992 | Pinchuk |
| 5,261,916 A | * | 11/1993 | Engelson .................... 606/108 |
| 5,354,295 A | * | 10/1994 | Guglielmi et al. ............. 606/32 |
| 5,382,259 A | * | 1/1995 | Phelps et al. ................ 606/151 |
| 5,551,954 A | | 9/1996 | Buscemi et al. |
| 5,690,671 A | * | 11/1997 | McGurk et al. ............. 606/200 |
| 5,911,731 A | | 6/1999 | Pham et al. |
| 5,964,797 A | * | 10/1999 | Ho .............................. 606/194 |
| 6,024,754 A | | 2/2000 | Engelson |
| 6,033,582 A | * | 3/2000 | Lee et al. ...................... 216/37 |
| 6,063,100 A | * | 5/2000 | Diaz et al. ................... 606/191 |
| 6,096,052 A | | 8/2000 | Callister et al. |
| 6,113,622 A | | 9/2000 | Hieshima |
| 6,165,198 A | * | 12/2000 | McGurk et al. ............. 606/200 |
| 6,231,590 B1 | * | 5/2001 | Slaikeu et al. .............. 606/200 |
| 6,280,457 B1 | * | 8/2001 | Wallace et al. ............. 606/200 |
| 6,299,627 B1 | * | 10/2001 | Eder et al. ................... 606/191 |
| 6,530,934 B1 | * | 3/2003 | Jacobsen et al. ............ 606/157 |
| 6,660,020 B2 | * | 12/2003 | Wallace et al. ............. 606/195 |
| 2001/0044629 A1 | * | 11/2001 | Stinson ....................... 606/108 |

FOREIGN PATENT DOCUMENTS

| | | |
|---|---|---|
| FR | 2 696 636 A | 4/1994 |
| WO | 98/02100 A1 | 1/1998 |

* cited by examiner

*Primary Examiner*—Henry Bennett
*Assistant Examiner*—Kathryn Odland
(74) *Attorney, Agent, or Firm*—George H. Gertsman; Seyfarth Shaw

(57) ABSTRACT

A method as provided for occluding the vasculature of a patient. The method comprises the steps of providing a plurality of embolic coils having a textured surface. The embolic coils are introduced into the patient's vasculature. In this manner, the textured surface provides improved platelet adhesion compared to a non-textured surface, to promote clotting. In the illustrative embodiment, the embolic coil comprises a platinum-tungsten alloy wire and the texturing is performed by abrasion or sandblasting to provide substantially uniform roughness comprising pockets having diameters of about 0.125 microns to about fifty microns and depths of about 0.25 microns to about twenty microns.

17 Claims, 3 Drawing Sheets

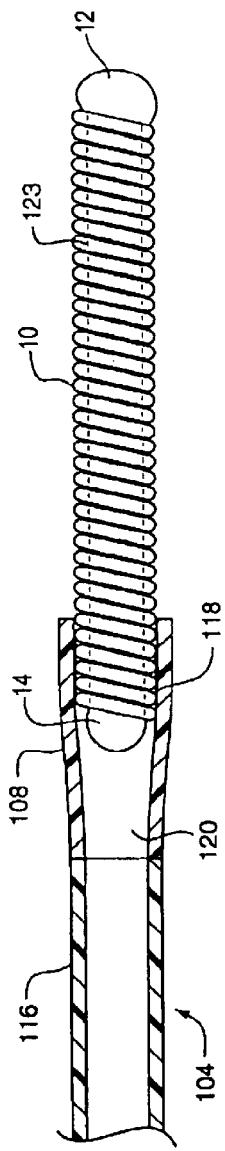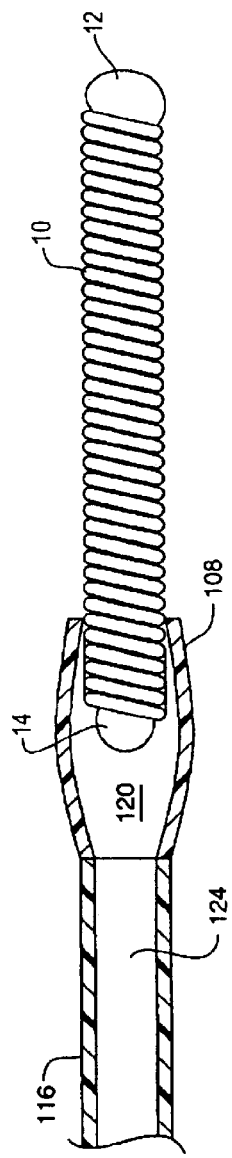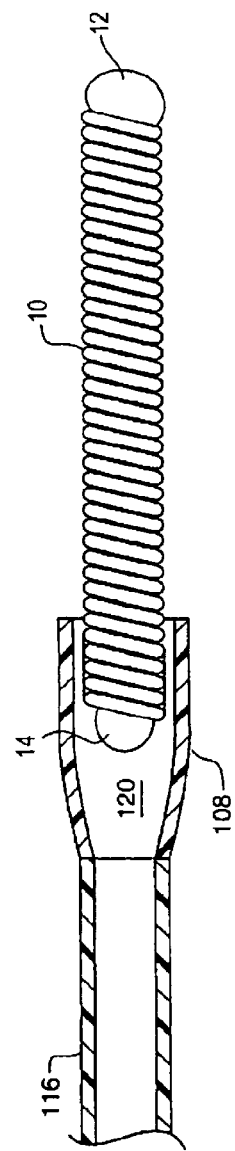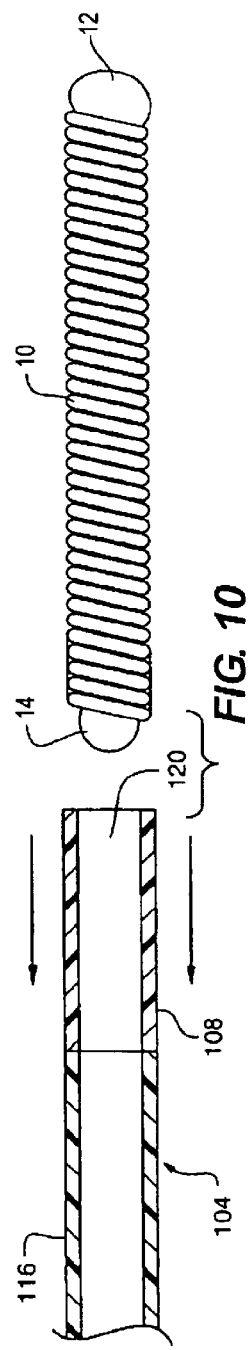

US 6,953,468 B2

OCCLUDING VASCULATURE OF A PATIENT USING EMBOLIC COIL WITH IMPROVED PLATELET ADHESION

FIELD OF THE INVENTION

The present invention concerns a novel method for occluding the vasculature of a patient and, more particularly, a method of treatment in which embolic coils are placed within the patient's vasculature.

BACKGROUND OF THE INVENTION

A known technique for treating a brain aneurysm of a patient includes the placement of embolic coils within the aneurysm. To this end, a catheter is introduced into the vessel leading to the aneurysm, and embolic coils are delivered to pack and fill the aneurysm. Ordinarily, a deployment system is used to deliver the coils, via the catheter, to the aneurysm, such as the deployment system disclosed in Hieshima U.S. Pat. No. 6,113,622, the disclosure of which is incorporated herein by reference.

The embolic coils act to reduce the blood flow inside of the aneurysm. Typically the embolic coils provide a mechanical blockage to the blood flow in the aneurysm. In this manner, the stagnation of blood that is obtained prevents the blood flow from rupturing the aneurysm. However, such stagnation forms a thrombus inside the aneurysm, that eventually can get resorbed.

We have discovered a method by which the desirable mechanical blockage of blood flow can be obtained with the addition of platelet adhesion to the embolic coils. This allows tissue to be able to grow, and the thrombus that forms, instead of being resorbed, has the ability to be organized into fibrous scar tissue. Such fibrous scar tissue achieves long term healing of the aneurysm in contrast to the use of embolic coils that can move around with the result that the formed thrombus may be resorbed.

The method that we have discovered is useful for occluding the vasculature of a patient. In addition to embolizing an aneurysm, the method of the present invention may also be used for embolizing a vessel for vessel sacrifice; for reducing or blocking blood flow to an arterial-venous malformation or to a fistula; and for blocking blood flow to tumors.

It is, therefore, an object of the present invention to provide a novel method for occluding the vasculature of a patient using implanted embolic coils in which there is improved platelet adhesion to the coils.

A further object of the present invention to provide a novel method for treating an aneurysm of a patient using implanted embolic coils in which there is improved platelet adhesion to the coils.

Another object of the present invention is to provide a novel method for treating an aneurysm of a patient using embolic coils and enabling tissue formation to prevent the coils from moving around within the aneurysm.

A further object of the present invention is to provide a novel embolic coil that is simple in construction and easy to manufacture.

A still further object of the present invention is to provide a novel embolic coil which provides improved platelet adhesion.

Other objects and advantages of the present invention will become apparent as the description proceeds.

SUMMARY OF THE INVENTION

In accordance with the present invention, a method is provided for occluding the vasculature of a patient. The method comprises the steps of providing a plurality of embolic coils having a textured surface. The plurality of embolic coils having a textured surface are introduced into the patient's vasculature. In this manner, the textured surface provides improved platelet adhesion compared to a non-textured surface, to promote clotting.

In the illustrative embodiment, the surface of the embolic coils are textured by abrasion or sandblasting. The embolic coil comprises a platinum-tungsten alloy wire and in a specific example, the embolic coils have a substantially uniform roughness comprising pockets having diameters of between about 0.125 microns and about 50 microns and depths between about 0.25 microns to 20 microns.

A more detailed explanation of the invention is provided in the following description and claims, and is illustrated in the accompanying drawings.

BRIEF DESCRIPTION OF THE DRAWINGS

FIG. 7 is an enlarged partially sectional view showing the distal end of a coil deployment system prior to deployment of the coil.

FIGS. 8 and 9 illustrate the sequential steps in the radial expansion of the distal tip of the coil deployment system as the embolic coil is released.

FIG. 10 illustrates the distal tip of the coil deployment system after release of the embolic coil.

DETAILED DESCRIPTION OF THE ILLUSTRATIVE EMBODIMENT

Figure 1:
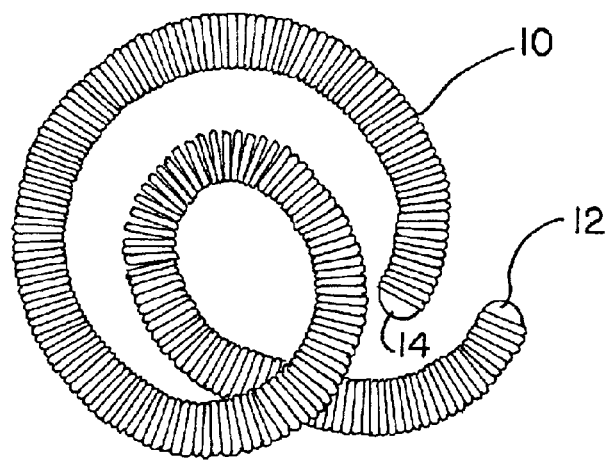
FIG. 1 is a view of an embolic coil constructed in accordance with the principles of the present invention.

Referring to the drawings, in FIG. 1 there is shown an embolic coil constructed in accordance with the principles of the present invention. Embolic coil 10 is formed by winding a platinum-tungsten alloy wire into a helical configuration. In the illustrative embodiment, the diameter of the wire is generally in the range of about 0.0015 to 0.008 inches. The outside diameter of the coil 10 is preferably in the range of about 0.006 to 0.055 inches. The embolic coil 10 shown in FIG. 1 may be straight or may take the form of various configurations, including the form of a helix, a random shape configuration, or a coil within a coil configuration.

The details of construction of an example embolic coil, although no limitation is intended, is disclosed in Diaz et al. U.S. Pat. No. 6,063,100, issued May 16, 2000, the disclosure of which is incorporated herein by reference.

With the helical wound coil as illustrated in FIG. 1, the coil is provided with a seal plug 12 at its distal end and another seal plug 14 at its proximal end. Seal plugs 12 and 14 serve to prevent the flow of fluid through the lumen of the coil 10.

Although no limitation is intended, as a specific example coil 10 is formed of a platinum-tungsten alloy comprising 92% platinum and 8% tungsten. In accordance with the present invention, the outer surface of the coil is textured by abrasion or sandblasting. To this end, fifty-micron diameter alumina particles are used to texture the surface of the wire that is used to form the coils, prior to the formation of the helical coils. It has been found that the textured surface provides improved platelet adhesion thus promoting clotting and subsequent endothelialization.

Although no limitation is intended, as a specific example the texturization provides a uniform roughness comprising pockets having diameters of between about 0.125 microns and about 50 microns and depths of between about 0.25 microns and about 20 microns. The roughness is uniform throughout the coil except if the coil is used with a detachment system such as disclosed in Hieshima U.S. Pat. No. 6,113,622 or Diaz et al. U.S. Pat. No. 6,063,100, a proximal portion of the coil is not textured in order for it to have a proper seal with a gripper so that it can released easily.

FIGS. 7–10 illustrate the detachment system disclosed in Hieshima U.S. Pat. No. 6,113,622. Referring to FIG. 7, the distal end of introducer 104 is illustrated in detail. Introducer 104 includes a proximal section 116 and a distal section 108. The proximal section 118 of the embolic coil 10 is disposed within the distal section 108 of the introducer and is tightly held within the lumen 120 of the distal section 108 prior to release of the coil.

Figure 3:
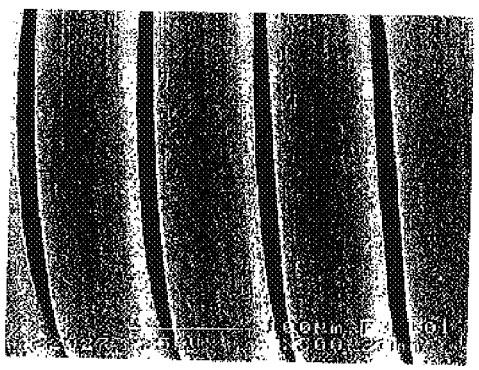
FIG. 3 is a photomicrograph, enlarged 233×, showing a portion of an embolic coil with a smooth surface, prior to texturing.
Figure 4:
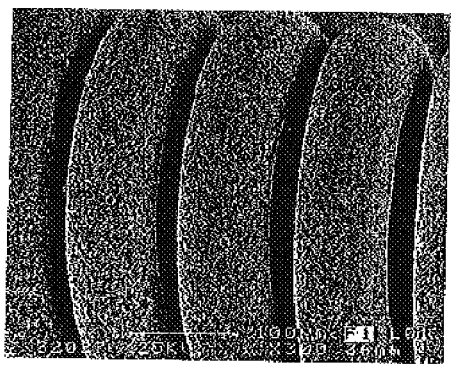
FIG. 4 is a photomicrograph, enlarged 233×, showing a similar portion of an embolic coil as the FIG. 3 portion, but with texturing.

FIGS. 3 and 4 generally illustrate the coil release mechanism in action for the deployment system. As shown in FIG. 3, when a hydraulic pressure is applied to the interior 124 of the introducer 104, the distal section 108 of the catheter begins to expand radially, much as a balloon expands during the process of inflation. As distal section 108 continues to expand radially there comes a point as illustrated in FIG. 9 in which the coil 10 become disengaged from the lumen of the distal section 108 and the coil 10 is then released from the introducer and is deployed at that location within the vessel. As illustrated in FIG. 10, when coil 10 has been released from introducer 104, the introducer may then be withdrawn leaving the coil 10 positioned at the desired site.

Figure 2:
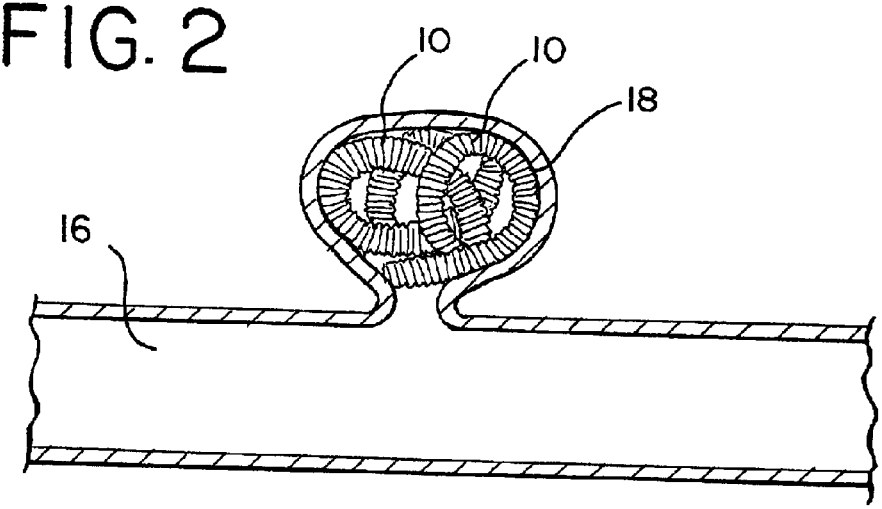
FIG. 2 is a diagram of a patient's brain aneurysm having the coils of the present invention implanted therein.

FIG. 2 is a diagrammatic view of a patient's vessel 16 leading to an aneurysm 18 into which a number of embolic coils 10 have been introduced. The coils are introduced in a manner known in the art, by introducing a catheter into the vessel 16, then introducing a deployment device via the catheter to deliver the embolic coils, one by one, to the aneurysm 18.

Figure 5:
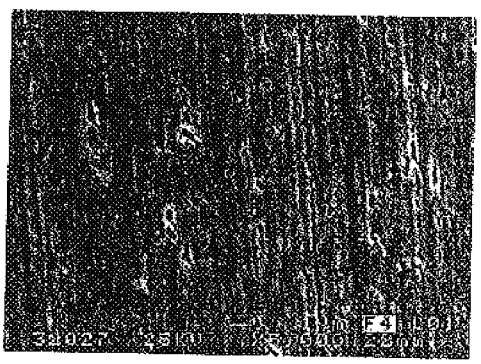
FIG. 5 is a photomicrograph, enlarged 3880×, showing a portion of an embolic coil with a smooth surface, prior to texturing.
Figure 6:
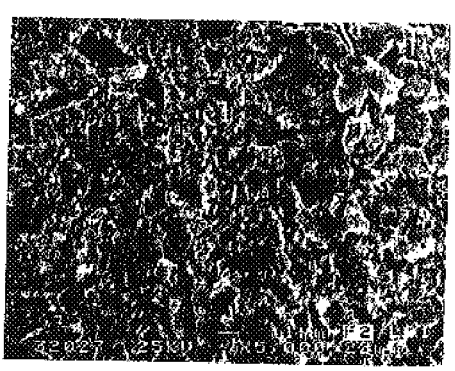
FIG. 6 is a photomicrograph, enlarged 3880×, showing a similar portion of an embolic coil as the FIG. 5 portion, but with texturing.

SEM micrographs of the non-textured vs. textured coils are provided in FIGS. 3–6. Referring to FIG. 3, a portion of a non-textured coil is shown in a micrograph having an enlargement of 233×. FIG. 4 shows a similar coil with a 233× enlargement, but with texture that has been provided by sandblasting as disclosed above. FIG. 5 is a greatly enlarged micrograph, having an enlargement of 3880×, of the coil sample of FIG. 3 and FIG. 6 is a greatly enlarged micrograph having an enlargement of 3880×, of the coil sample of FIG. 5.

Testing was conducted using radiolabeled platelets to evaluate an ex vivo aneurysm model. In the model, aneurysms treated with textured coils were compared to aneurysms treated with non-textured coils. The textured coils showed an increased in the platelet deposition of about fifty percent over the non-texture coils.

It can be seen that by using embolic coils that have been textured, there is superior platelet adhesion which promotes clotting and subsequent endothelialization. A texturing technique has been disclosed that is simple and does not require expensive or elaborate equipment to modify the coils. In the illustrative embodiment the texturing technique does not require coating or ion implantation, thereby avoiding the importation of any new materials to the coil that would require new biocompatability testing.

Although an illustrative embodiment of the invention has been shown and described, it is to be understood that various modifications and substitutions may be made by those skilled in the art without departing from the novel spirit and scope of the present invention.

What is claimed is:

1. A embolic coil formed of a platinum alloy wire and having a proximal portion which is adopted to be held by a detachment portion of an introducer and a distal portion, the proximal portion which is adopted to be held by a detachment portion of an introducer having a relatively smooth surface as compared to the surface of the distal portion and the distal portion having a relatively textured surface as compared to the smooth surface of the proximal portion, whereby when said embolic coil is implanted in a patient's vasculature, the textured surface provides improved platelet adhesion compared to a non-textured surface, to promote clotting.

2. An embolic coil as defined in claim 1, in which said distal portion has substantially uniform roughness comprising pockets having diameters between about 0.125 microns and about fifty microns and depths between about 0.25 microns and twenty microns.

3. A method for occluding the vasculature of a patient, comprising the steps of:

providing an introducer having a detachment portion for holding and releasing an embolic coil;

providing a plurality of embolic coils having a proximal portion that is held by said detachment portion and a distal portion, the proximal portion that is held by said detachment portion having a relatively smooth surface as compared to the surface of the distal portion and the distal portion having a relatively textured surface as compared to the smooth surface of the proximal portion;

introducing said plurality of embolic coils into the patients vasculature, using said introducer that is coupled to the proximal portion, whereby the textured surface provides improved platelet adhesion compared to a non-textured surface, to promote clotting.

4. A method as defined in claim 3, including the step of texturing the surface of an embolic coil by abrasion.

5. A method as defined in claim 3, including the step of texturing the surface of an embolic coil by sandblasting.

6. A method as defined in claim 3, in which said embolic coil comprises a platinum-tungsten alloy wire.

7. A method as defined in claim 1, in which the distal portion of said embolic coil has substantially uniform roughness comprising pockets having diameters between about 0.125 microns and about 50 microns.

8. A method as defined in claim 7, in which said pockets have depths of between about 0.25 microns and about 20 microns.

9. A method as defined in claim 3, in which the embolic coils are used to embolize a vessel for vessel sacrifice.

10. A method as defined in claim 3, in which the embolic coils are used to reduce or block blood flow to an arterial-venous malformation or to a fistula.

11. A method as defined in claim 1, in which the embolic coils are used to block blood flow to a tumor.

12. A method for treating an aneurysm of a patient, comprising the steps of:

providing an introducer having a detachment portion for holding and releasing an embolic coil;

providing a plurality of embolic coils having a proximal portion that is held by said detachment portion and a distal portion, the proximal portion that is held by said detachment portion having a relatively smooth surface as compared to the surface of the distal portion and the distal portion having a relatively textured surface as compared to the smooth surface of the proximal portion;

introducing said plurality of embolic coils into the patient's aneurysm, using said introducer that is coupled to the proximal portion, whereby the textured surface provides improved platelet adhesion compared to a non-textured surface, to promote clotting.

13. A method as defined in claim 12, including the step of texturing the surface of an embolic coil by abrasion.

14. A method as defined in claim 12, including the step of texturing the surface of an embolic coil by sandblasting.

15. A method as defined in claim 12, in which said embolic coil comprises a platinum-tungsten alloy wire.

16. A method as defined in claim 12, in which the distal portion of said embolic coil has substantially uniform roughness comprising pockets having diameters between about 0.125 microns and about 50 microns.

17. A method as defined in claim 12, in which said pockets have depths of between about 0.25 microns and about 20 microns.

* * * * *